US010870631B2

(12) United States Patent
Hofen et al.

(10) Patent No.: US 10,870,631 B2
(45) Date of Patent: Dec. 22, 2020

(54) PROCESS FOR THE EPOXIDATION OF PROPENE

(71) Applicants: EVONIK OPERATIONS GMBH, Essen (DE); thyssenkrupp Industrial Solutions AG, Essen (DE)

(72) Inventors: Willi Hofen, Rodenbach (DE); Thomas Haas, Münster (DE); Wolfgang Wöll, Maintal (DE); Jürgen Schemel, Bad Soden (DE); Hans-Christian Dietz, Hattersheim (DE); Marc Brendel, Bruchköbel (DE)

(73) Assignees: EVONIK OPERATIONS GMBH, Essen (DE); THYSSENKRUPP INDUSTRIAL SOLUTIONS AG, Essen (DE)

( * ) Notice: Subject to any disclaimer, the term of this patent is extended or adjusted under 35 U.S.C. 154(b) by 0 days.

(21) Appl. No.: 16/615,720

(22) PCT Filed: May 16, 2018

(86) PCT No.: PCT/EP2018/062748
§ 371 (c)(1),
(2) Date: Nov. 21, 2019

(87) PCT Pub. No.: WO2018/215262
PCT Pub. Date: Nov. 29, 2018

(65) Prior Publication Data
US 2020/0109125 A1      Apr. 9, 2020

(30) Foreign Application Priority Data

May 22, 2017  (EP) .................................... 17172167

(51) Int. Cl.
C07D 301/12        (2006.01)

(52) U.S. Cl.
CPC .................................. *C07D 301/12* (2013.01)

(58) Field of Classification Search
CPC .................................................... C07D 301/12
(Continued)

(56) References Cited

U.S. PATENT DOCUMENTS

| 4,308,409 A | 12/1981 | Wu et al. |
| 5,274,140 A | 12/1993 | Venturello et al. |

(Continued)

FOREIGN PATENT DOCUMENTS

| DE | 195 07 584 | 9/1996 |
| EP | 0 100 119 | 2/1984 |

(Continued)

OTHER PUBLICATIONS

International Search Report for corresponding PCT/EP2018/062748 filed May 16, 2018.

(Continued)

*Primary Examiner* — Taylor V Oh
(74) *Attorney, Agent, or Firm* — Law Office of: Michael A. Sanzo, LLC

(57) ABSTRACT

In a process for the epoxidation of propene, comprising continuously reacting a propene feed with hydrogen peroxide in the presence of an epoxidation catalyst in a reaction step, using propene in excess to hydrogen peroxide, to provide a liquid reaction mixture comprising non-reacted propene, extra safety measures caused by the presence of oxygen during work-up of the liquid reaction mixture of the epoxidation reaction can be avoided by stripping liquid reaction mixture from step a) with an inert gas to provide an oxygen depleted stripped liquid reaction mixture and a strip gas stream, selecting the amount of inert gas to provide an oxygen concentration in the strip gas stream in the range of from 0.1 to 10% by weight, separating non-reacted propene (Continued)

from the strip gas stream and recycling it to the reaction step, and separating propene oxide from the stripped liquid reaction mixture.

20 Claims, 3 Drawing Sheets

(58) Field of Classification Search
USPC .......................................................... 549/531
See application file for complete search history.

(56) References Cited

U.S. PATENT DOCUMENTS

| | | | |
|---|---|---|---|
| 5,591,875 | A | 1/1997 | Chang et al. |
| 5,599,956 | A | 2/1997 | Pujado et al. |
| 6,372,924 | B2 | 4/2002 | Thiele |
| 6,673,950 | B1 | 1/2004 | Teles et al. |
| 6,861,042 | B2 | 3/2005 | Korl et al. |
| 6,881,853 | B2 | 4/2005 | Teles et al. |
| 7,169,945 | B2 | 1/2007 | Haas et al. |
| 7,173,143 | B2 | 2/2007 | Bender et al. |
| 7,601,263 | B2 | 10/2009 | Ebert et al. |
| 7,658,893 | B2 | 2/2010 | Bassler et al. |
| 7,670,572 | B2 | 3/2010 | Porscha et al. |
| 7,833,498 | B2 | 11/2010 | Goebbel et al. |
| 7,863,211 | B2 | 1/2011 | Strebelle et al. |
| 8,545,673 | B2 | 10/2013 | Dietz et al. |
| 9,539,549 | B2 | 1/2017 | Haensel et al. |
| 10,053,438 | B2 | 8/2018 | Bolz et al. |
| 10,053,440 | B2 | 8/2018 | Bolz et al. |
| 10,087,158 | B2 | 10/2018 | Stock et al. |
| 10,100,024 | B2 | 10/2018 | Stochniol et al. |
| 10,125,108 | B2 | 11/2018 | Jahn et al. |
| 10,196,370 | B2 | 2/2019 | Stock et al. |
| 10,214,471 | B2 | 2/2019 | Wiederhold et al. |
| 10,214,504 | B2 | 2/2019 | Brendel et al. |
| 10,399,952 | B2 | 9/2019 | Wöll et al. |
| 10,428,035 | B2 | 10/2019 | Pascaly et al. |
| 10,428,036 | B2 | 10/2019 | Hofen et al. |
| 10,597,374 | B2 | 3/2020 | Wiederhold et al. |
| 10,676,450 | B2 | 6/2020 | Schmidt et al. |
| 2003/0040637 | A1 | 2/2003 | Hofen et al. |
| 2003/0212282 | A1 | 11/2003 | Hofen et al. |
| 2005/0245751 | A1 | 11/2005 | Bender et al. |
| 2006/0014970 | A1 | 1/2006 | Goebbel et al. |
| 2006/0058539 | A1 | 3/2006 | Babler et al. |
| 2007/0004926 | A1 | 1/2007 | Schindler et al. |
| 2012/0142950 | A1 | 6/2012 | Teles et al. |
| 2015/0007951 | A1 | 1/2015 | Dietz et al. |
| 2018/0030010 | A1 | 2/2018 | Breitenbach et al. |
| 2018/0057473 | A1 | 3/2018 | Stock et al. |
| 2019/0023673 | A1 | 1/2019 | Schmidt et al. |
| 2019/0276419 | A1 | 9/2019 | Wiederhold et al. |

FOREIGN PATENT DOCUMENTS

| | | |
|---|---|---|
| EP | 0 230 949 | 8/1987 |
| EP | 0 659 473 | 6/1995 |
| EP | 0 719 768 | 7/1996 |
| EP | 0 757 045 | 2/1997 |
| EP | 1 247 806 | 10/2002 |
| EP | 1 489 074 | 12/2004 |
| EP | 2 014 654 | 1/2009 |
| WO | WO 99/07690 | 2/1999 |
| WO | WO 01/57010 | 8/2001 |
| WO | WO 02/085873 | 10/2002 |
| WO | WO 03/016296 | 2/2003 |
| WO | WO 03/018567 | 3/2003 |
| WO | WO 03/093255 | 11/2003 |
| WO | WO 2004/018088 | 3/2004 |
| WO | WO 2004/028962 | 4/2004 |
| WO | WO 2004/048335 | 6/2004 |
| WO | WO 2004/048354 | 6/2004 |
| WO | WO 2004/048355 | 6/2004 |
| WO | WO 2005/000827 | 1/2005 |
| WO | WO 2005/103024 | 11/2005 |
| WO | WO 2008/118265 | 10/2008 |
| WO | WO 2008/141734 | 11/2008 |
| WO | WO 2011/063937 | 6/2011 |
| WO | WO 2016/016070 | 2/2016 |
| WO | WO 2017/089079 | 6/2017 |

OTHER PUBLICATIONS

Written Opinion of the International Searching Authority for corresponding PCT/EP2018/062748 filed May 16, 2018.
International Preliminary Report on Patentability for corresponding PCT/EP2018/062748 filed May 16, 2018.
European Search Report and Opinion for for corresponding European application EP 17 17 2167 filed May 22, 2017.
Chowdhury, et al, "Recovery of Homogeneous Polyoxometallate Catalysts from Aqueous and Organic Media by a Mesoporous Ceramic Membrane without Loss of Catalytic Activity," *Chem. Eur. J.* 12(11):3061-3066 (Apr. 2006).
Guojie, et al., "Factors Affecting Propylene Epoxidation Catalyzed by Reaction-Controlled Phase-Transfer Catalyst," *Chinese Journal of Catalysis* 26:1005-1010 (Nov. 2005), with English language abstract on p. 1 of the article.
Kaur, et al., "Poloxometalate-catalysed epoxidation of propylene with hydrogen peroxide: microemulsion versus biphasic process," *Catalysis Communications* 5(11): 709-713 (Nov. 2004).
Li, et al., "Influence of composition of heteropolyphophatotungstate catalyst on epoxidation of propylene," *Journal of Molecular Catalysis A: Chemical* 218(2):247-252 (Aug. 2004).
Luthra, et al., "Homogeneous phase transfer catalyst recovery and re-use using solvent resistant membranes," *Journal of Membrane Science* 201:65-75 (2002).
Shin, et al., "Kinetics of Heterogeneous Catalytic Epoxidation of Propene with Hydrogen Peroxide over Titanium Silicalite (TS-I)," *Ind. Eng. Chem. Res.* 49:8125-8134 (published on Web Jul. 27, 2010).
Ullmanns Encylopedia of Industrial Chemistry, online edition 2013, entry "propene," DOI 10.1002/14356007.a22_211.pub3.
Venturello, et al., "A New, Effective Catalytic System for Epoxidation of Olefins by Hydrogen Peroxide under Phase-Transfer Conditions," *J. Org. Chem.* 48:3831-3833 (1983).
Wang, et al., "Epoxidation of Propylene Over Titanosilicate-1 in Fixed-bed Reactor: Experiments and Kinetics," *Asian Journal of Chemistry* 26(4):9430950 (online Feb. 15, 2014).
U.S. Appl. No. 16/070,873, filed Jul. 18, 2018, US-2019/0023673 A1, Jan. 24, 2019, Schmidt.
U.S. Appl. No. 16/302,099, filed Nov. 15, 2018, US-2019/0276419 A1, Sep. 12, 2019, Wiederhold.

PROCESS FOR THE EPOXIDATION OF PROPENE

CROSS REFERENCE TO RELATED APPLICATIONS

The present application is US national stage of international application PCT/EP2018/062748, which had an international filing date of May 16, 2018 and which was published on Nov. 29, 2018. Priority is claimed to European application EP 17172167.3, filed on May 22, 2017.

PARTIES TO A JOINT RESEARCH AGREEMENT

The presently-claimed invention was made by or on behalf of the below listed parties to a Joint Research Agreement. The Joint Research Agreement was in effect on or before the date the claimed invention was made, and the claimed invention was made as a result of activities undertaken within the scope of the Joint Research Agreement. The parties to the Joint Research Agreement are Evonik Operations GmbH and thyssenkrupp Industrial Solutions AG. The Agreement was signed on Aug. 22, 2000 by Degussa-Hüls AG and Krupp Uhde GmbH and and is still in force. Evonik Operations GmbH (renamed from Evonik Degussa GmbH) is the legal successor to Degussa-Hüls AG and thyssenkrupp Industrial Solutions AG is the legal successor to Krupp Uhde GmbH.

FIELD OF THE INVENTION

The present invention relates to a process for the continuous epoxidation of propene with hydrogen peroxide in the presence of an epoxidation catalyst, where non-reacted propene is recovered and recycled to the epoxidation reaction.

BACKGROUND OF THE INVENTION

The epoxidation of propene with hydrogen peroxide in the presence of an epoxidation catalyst is usually carried out with a molar excess of propene relative to hydrogen peroxide in order to avoid hydrogen peroxide decomposition and to achieve high selectivities for propene oxide. The reaction is usually carried out at a pressure of more than 1.0 MPa to achieve high propene concentrations in the liquid phase reaction mixture. Epoxidation of propene with a heterogeneous titanium silicalite catalyst is known from EP 0 100 119 A1.

For an efficient use of propene, non-reacted propene has to be recovered from the liquid reaction mixture of the epoxidation reaction and recycled to the epoxidation reaction.

EP 0 719 768 A1 describes recovery of non-reacted propene by a distillation where essentially all propene oxide remains in the bottoms product.

WO 99/07690 suggests to substantially remove unreacted propene from an epoxidation reaction product by distillation such as a flash distillation.

WO 2008/118265 A1 teaches that two depropanization columns running at low and high pressures are required to effectively separate propane and propene from the epoxidation reaction mixture without significant loss of propene oxide. As an alternative, a combination of a flash separator and an extractive distillation using methanol and/or water as extractive distillation solvent is proposed.

WO2005/103024 describes recovery of non-reacted propene by distillation at low pressure, preferably in a single column, providing a propene rich vapor as overhead product, compressing this vapor in two or three compression stages and absorbing propene from the compressed vapor with a liquid absorbent.

WO 01/57010 describes recovery of non-reacted propene by a pressure release stage, recompressing the gas obtained in this stage to the pressure prevailing in the epoxidation reactor and returning the gas to the reaction. Further propene can be recovered in vapor form by a subsequent separation of the liquid obtained in the pressure release stage in a pre-evaporator, partial condensation of the overhead product obtained in the pre-evaporator and recompression of the uncondensed propene.

The prior art processes for recovering non-reacted propene from the liquid reaction mixture of the epoxidation reaction by distillation or by a sequence of pressure reduction, recompression and condensation all suffer from the disadvantage that the liquid reaction mixture from the epoxidation reaction contains oxygen formed by decomposition of hydrogen peroxide during the epoxidation reaction and this oxygen gets enriched in the vapor phase that remains when propene is condensed in a distillation or condensation step. Therefore, the prior art processes require extra measures to prevent formation of explosive vapor mixtures during these steps, such as monitoring oxygen content of the vapor phase and adding inert gas prior to condensation. Addition of inert gas reduces the efficiency of condensers and thus requires condensers of increased size for recovering the non-reacted propene.

WO 03/08401 describes an epoxidation process, where all the non-reacted propene is evaporated from the liquid reaction mixture and the resulting gas mixture comprising propene and oxygen is brought into contact with a liquid solvent to absorb propene from the mixture. The absorption conditions are controlled to obtain an off gas which contains propene in an amount sufficient to render the off gas non-flammable despite its oxygen content. This process has the disadvantage that a substantial fraction of the non-reacted propene is lost with the off gas and cannot be reused for epoxidation.

SUMMARY OF THE INVENTION

It has now been found that problems and extra safety measures caused by the presence of oxygen during work-up of the liquid reaction mixture of the epoxidation reaction can be avoided by stripping the liquid reaction mixture with an inert gas before carrying out separation of propene oxide and non-reacted propene by distillation or pressure reduction steps.

Recovery of propene from the strip gas stream by absorption in a solvent and passing the propene loaded solvent to the epoxidation reaction also allows for recovering a part of the non-reacted propene without requiring energy for recompression or for refrigeration to condense propene.

Subject of the invention is therefore a process for the epoxidation of propene, comprising a) continuously reacting a propene feed with hydrogen peroxide in the presence of an epoxidation catalyst in a reaction step, using propene in excess to hydrogen peroxide, to provide a liquid reaction mixture comprising non-reacted propene;

b) stripping liquid reaction mixture from step a) with an inert gas in a counter-current stripping column to provide an oxygen depleted stripped liquid reaction mixture and a strip gas stream, selecting the amount of inert gas to provide an oxygen concentration in the strip gas stream in the range of from 0.1 to 10% by weight, preferably of from 0.5 to 8% by weight;
c) separating non-reacted propene from the strip gas stream obtained in step b) and recycling it to step a); and
d) separating propene oxide from the stripped liquid reaction mixture obtained in step b).

DETAILED DESCRIPTION OF THE INVENTION

Figure 1:
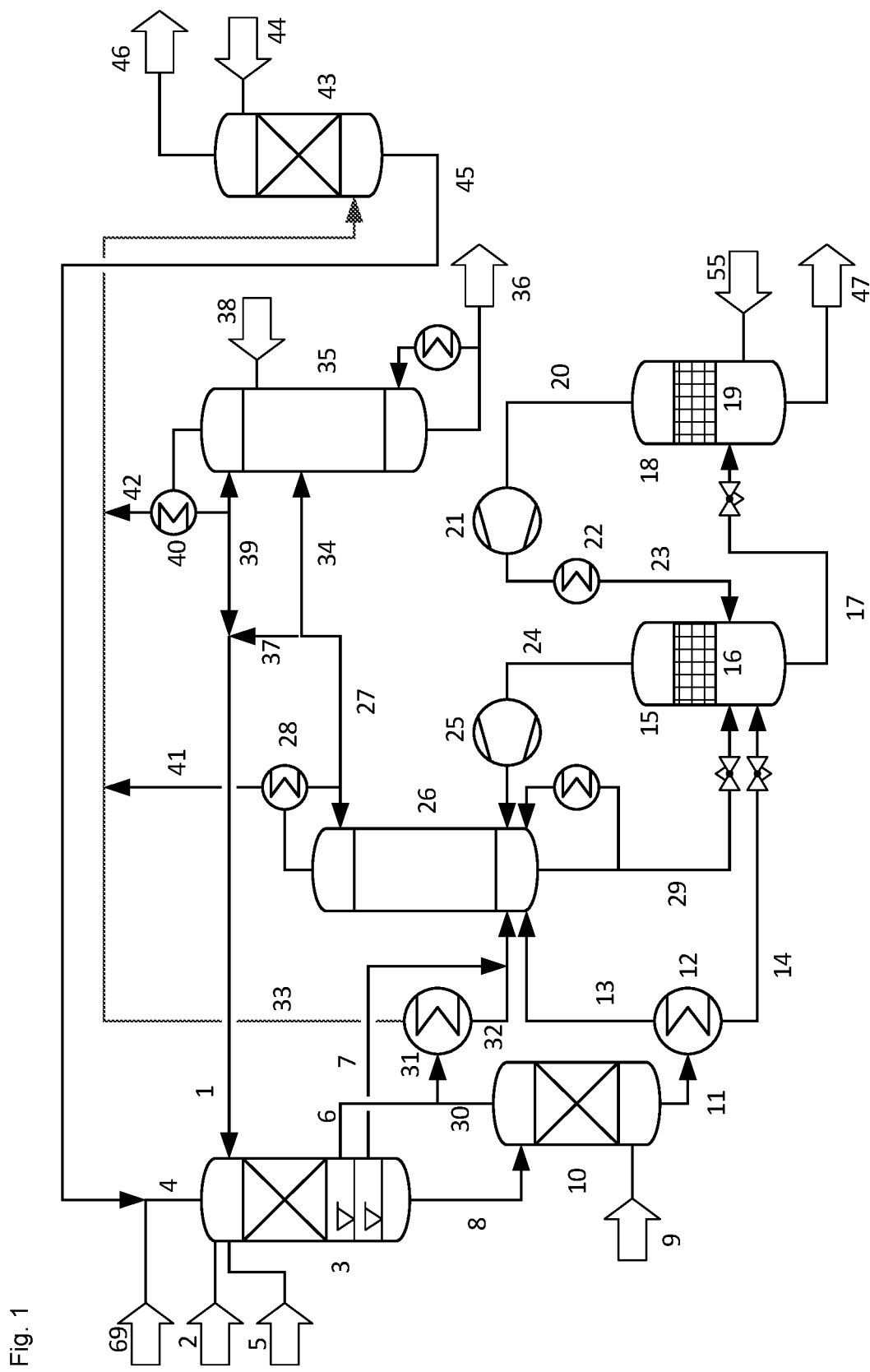
FIGS. 1 and 2 show a preferred embodiment of the process of the invention where propene oxide and part of the propene are condensed from the strip gas before propene is absorbed into a methanol solvent.

All pressure values refer to absolute pressure in Megapascal (MPa).

In step a) of the process of the invention, a propene feed is continuously reacted in a reaction step with hydrogen peroxide in the presence of an epoxidation catalyst to provide a liquid reaction mixture containing propene oxide and non-reacted propene. The reaction is carried out using propene in excess to hydrogen peroxide. Propene is preferably used at a molar ratio of propene to hydrogen peroxide of from 1.1:1 to 30:1, more preferably 2:1 to 10:1 and most preferably 3:1 to 5:1. Propene is preferably used in an excess sufficient to maintain an additional liquid phase rich in propene throughout step a). The pressure in step a) is preferably at least 1.9 MPa, more preferably from 1.9 to 5.0 MPa, even more preferably 2.1 to 3.6 MPa and most preferably 2.4 to 2.8 MPa. Using an excess of propene at a high pressure provides high reaction rate and hydrogen peroxide conversion and at the same time high selectivity for propene oxide.

The propene feed may contain propane, preferably with a molar ratio of propane to propene of from 0.001 to 0.15 and more preferably of from 0.08 to 0.12. Hydrogen peroxide can be used as an aqueous solution, preferably containing from 30 to 75% by weight hydrogen peroxide and most preferably from 40 to 70% by weight. The aqueous hydrogen peroxide solution is preferably made by an anthraquinone process.

The epoxidation catalyst can be a homogeneous catalyst or a heterogeneous catalyst. Suitable homogeneous epoxidation catalysts are manganese complexes with polydentate nitrogen ligands, in particular 1,4,7-trimethyl-1,4,7-triazacyclononane ligands, as known from WO 2011/063937. Other suitable homogeneous epoxidation catalysts are heteropolytungstates and heteropolymolybdates, in particular polytungstophosphates, as known from U.S. Pat. No. 5,274,140. Suitable heterogeneous epoxidation catalysts are titanium zeolites containing titanium atoms on silicon lattice positions. Preferably, a titanium silicalite catalyst is used, preferably with an MFI or MEL crystal structure. Most preferably a titanium silicalite 1 catalyst with MFI structure as known from EP 0 100 119 A1, is used. The titanium silicalite catalyst is preferably employed as a shaped catalyst in the form of granules, extrudates or shaped bodies. The shaped catalyst may contain 1 to 99% by weight of a binder or carrier material, all binders and carrier materials being suitable that do not react with hydrogen peroxide or with propene oxide under the reaction conditions employed for the epoxidation, silica being preferred as binder. Extrudates with a diameter of 1 to 5 mm are preferably used as shaped bed catalysts.

The reaction of the olefin with hydrogen peroxide can be carried out in the absence or in the presence of a solvent. The reaction is preferably carried out in the presence of a solvent when the epoxidation catalyst is a titanium zeolite. Suitable are all solvents which are not oxidized or are oxidized to only a small extent by hydrogen peroxide under the reaction conditions chosen and which dissolve in water in an amount of more than 10% by weight. Solvents which are completely miscible with water are preferred. Particularly suitable solvents are alcohols, such as methanol, ethanol or tert-butanol; glycols, such as ethylene glycol, 1,2-propanediol or 1,3-propanediol; cyclic ethers, such tetrahydrofuran, dioxane or propylene oxide; glycol ethers, such ethylene glycol monomethyl ether, ethylene glycol monoethyl ether, ethylene glycol monobutyl ether or the propylene glycol monomethyl ethers; ketones, such as acetone or 2-butanone; and nitriles, such as acetonitrile and propionitrile. The solvent is preferably used in the epoxidation in a weight ratio of 0.5 to 20 relative to the combined weight of water and hydrogen peroxide.

When the epoxidation catalyst is a titanium silicalite, the propene feed is preferably reacted with hydrogen peroxide in a methanol solvent to provide a liquid reaction mixture comprising methanol. The methanol solvent can be a technical grade methanol, a solvent stream recovered in the work-up of the epoxidation reaction mixture or a mixture of both. The methanol solvent may comprise other solvents in minor amounts, such as ethanol, with the amount of such other solvents preferably being less than 2% by weight. The methanol solvent may also comprise water, preferably from 2 to 13% by weight water. With a titanium silicalite catalyst the epoxidation reaction is preferably carried out at a temperature of 30 to 80° C., more preferably at 40 to 60° C.

The epoxidation reaction is preferably carried out with addition of ammonia to improve propene oxide selectivity as described in EP 0 230 949 A2. Ammonia is preferably added in an amount of from 100 to 3000 ppm based on the weight of hydrogen peroxide. The epoxidation is preferably carried out in a fixed bed reactor by passing a mixture comprising propene, hydrogen peroxide and methanol over a fixed bed comprising a shaped titanium silicalite catalyst. The fixed bed reactor is preferably equipped with cooling means and cooled with a liquid cooling medium. The temperature profile within this reactor is preferably maintained such that the cooling medium temperature of the cooling means is at least 20° C. and the maximum temperature within the catalyst bed is 60° C. at the most, preferably 55° C. Preferably, the temperature distribution along the length of the catalyst fixed bed is adjusted to keep the reaction temperature along 70 to 98%, preferably along 80 to 95%, of the length of the catalyst fixed bed within a range of less than 5° C., preferably within a range of from 0.5 to 3° C. The epoxidation reaction mixture is preferably passed through the catalyst bed in down flow mode, preferably with a superficial velocity from 1 to 100 m/h, more preferably 5 to 50 m/h, most preferred 5 to 30 m/h. The superficial velocity is defined as the ratio of volume flow rate/cross section of the catalyst bed. Additionally it is preferred to pass the reaction mixture through the catalyst bed with a liquid hourly space velocity (LHSV) from 1 to 20 h$^{-1}$, preferably 1.3 to 15 h$^{-1}$. It is particularly preferred to maintain the catalyst bed in a trickle bed state during the epoxidation reaction. Suitable conditions for maintaining the trickle bed state during the epoxidation reaction are disclosed in WO 02/085873 on page 8 line 23 to page 9 line 15. The amount of catalyst employed may be varied within wide limits and is preferably chosen so that a hydrogen peroxide consumption of more than 90%, preferably more than 95%, is achieved within 1 minute to 5 hours under the employed epoxidation reaction conditions. Most preferably, the epoxidation reaction is carried out with a catalyst fixed bed maintained in a trickle bed state at a pressure close to the vapor pressure of propene at the reaction temperature, using an excess of propene that provides a reaction mixture comprising two liquid phases, a methanol rich phase and a propene rich liquid phase. Two or more fixed bed reactors may be operated in parallel or in series in order to be able to operate the epoxidation process continuously when regenerating the epoxidation catalyst. Regeneration of the epoxidation catalyst can be carried out by calcination, by treatment with a heated gas, preferably an oxygen containing gas or by a solvent wash, preferably by the periodic regeneration described in WO 2005/000827. Regeneration of the epoxidation catalyst is preferably carried out without removing it from the fixed bed reactor. Different methods of regeneration may be combined.

In step b) of the process of the invention, liquid reaction mixture from step a) is stripped with an inert gas to provide an oxygen depleted stripped liquid reaction mixture and a strip gas stream. The inert gas is preferably selected from nitrogen, argon, oxygen depleted air, methane and mixtures thereof and is most preferably nitrogen. Stripping is carried out in a counter-current stripping column, in order to provide a stripped liquid reaction mixture which is essentially free of oxygen and preferably contains less than 300 ppm by weight oxygen. Stripping is preferably carried out at a temperature below the boiling point of propene at the pressure used in the stripping step in order to prevent propene from distilling off during stripping. The amount of inert gas is selected to provide an oxygen concentration in the strip gas stream in the range of from 0.1 to 10% by weight, preferably of from 0.5 to 8% by weight. Preferably, the oxygen concentration in the strip gas stream is measured continuously and the measured value is used to control the amount of inert gas used for stripping in order to maintain an essentially constant oxygen concentration in the strip gas stream.

Preferably, step a) is carried out at a reaction pressure of at least 1.9 MPa and the stripping of step b) is carried out at a pressure in the range of from 80% to 110% of the reaction pressure. Stripping at such a pressure removes only a small fraction of the non-reacted propene with the strip gas stream and keeps the major part of non-reacted propene in the stripped liquid reaction mixture. Non-reacted propene can then be recovered from the strip gas stream by absorption into a solvent with a small amount of solvent using a small sized absorption unit, in particular when absorption is carried out at the same pressure as step b) or at a pressure less than 1.0 MPa below the pressure used in step b).

In step c) of the process of the invention, non-reacted propene is separated from the strip gas stream obtained in step b) and recycled to step a). Non-reacted propene may be separated from the strip gas stream by condensation, preferably combined with further distillation of the condensate. In this case, the amount of inert gas is preferably selected to provide an oxygen concentration in the strip gas stream in the lower half of the claimed concentration range in order to prevent formation of flammable gas mixtures during propene condensation.

Preferably, the non-reacted propene is separated from the strip gas stream by contacting the strip gas stream with a liquid solvent to absorb propene into the solvent, providing a propene depleted gas stream and a propene loaded solvent. In this case, the amount of inert gas can be selected to provide an oxygen concentration in the strip gas stream near the upper end of the claimed concentration range in order to minimize the amount of inert gas used for the process. The absorption is preferably carried out in an absorption column which is preferably operated with counter-current flow. The absorption step is preferably carried out at a pressure in the range between the pressure used in step b) and 1.0 MPa lower than the pressure used in step b). The temperature in the absorption is preferably from 20 to 60° C., more preferably from 30 to 50° C. Propene may be desorbed from the propene loaded solvent by heating, by pressure reduction or a combination of both and the desorbed propene is then recycled to step a), optionally after condensing by cooling, compressing or a combination of both. More preferably, the propene loaded solvent is passed directly to step a). In this case, the solvent used in the reaction of step a) is preferably also used to absorb propene from the strip gas stream. When step a) is carried out with a titanium silicalite catalyst, the methanol solvent used in step a) is preferably used in step c) to absorb propene from the strip gas stream and the propene loaded methanol solvent is passed to step a).

In a preferred embodiment of step c), propene oxide is separated from the strip gas stream by partial condensation before the strip gas stream is contacted with a liquid solvent to absorb propene into the solvent and the propene loaded solvent is passed to step a). In this embodiment, the partial condensation is preferably carried out at a temperature where only a minor fraction of the propene contained in the strip gas stream is condensed along with propene oxide. Separation of propene oxide by partial condensation can improve propene oxide yields by preventing by-product formation from propene oxide recycled to step a).

In another preferred embodiment of step c), part of the propene contained in the strip gas stream is separated by condensation before the strip gas stream is contacted with a liquid solvent to absorb propene into the solvent and the propene loaded solvent is passed to step a). In this embodiment, condensation is preferably carried out at a low temperature to condense as much propene as possible. Condensing propene from the strip gas stream allows for operating the subsequent absorption with less cooling or can be used to reduce the size of the absorber and the amount of solvent needed for the subsequent absorption.

In a third preferred embodiment of step c), no component is separated from the strip gas stream before it is contacted with a liquid solvent to absorb propene into the solvent and the propene loaded solvent is passed to step a). This embodiment needs less equipment and less cooling capacity than the previous two embodiments, as it does not use cooling in a condenser.

In step d) of the process of the invention, propene oxide is separated from the stripped liquid reaction mixture obtained in step b). Preferably, non-reacted propene is also separated from the stripped liquid reaction mixture and is recycled to step a). The separation of propene oxide from the stripped liquid reaction mixture may be carried out by methods known from the prior art.

Preferably, the stripped liquid reaction mixture is subjected to a pressure reduction and propene vapor formed by the pressure reduction is recompressed and cooled to recover propene by condensation. The pressure reduction and vapor recompression is preferably carried out in several stages as described in patent application PCT/EP2016/076319. The compressed propene vapor is preferably fed to a propene distillation column and separated into an overhead product comprising non-reacted propene and a bottoms product containing compounds having a boiling point higher than propene, such as propene oxide and solvent. The overhead product comprising non-reacted propene can be recycled to the epoxidation reaction. The bottoms product can be combined with the liquid mixture remaining after the pressure reduction.

When a methanol solvent is used in step a), the liquid mixture remaining after the pressure reduction is preferably separated by distillation in a pre-separation column to provide a crude propene oxide comprising propene oxide, methanol and residual propene as an overhead product and a solvent mixture comprising methanol, water and peroxides as a bottoms product. The pre-separation column is preferably operated to provide an overhead product comprising from 20 to 60% of the methanol contained in the liquid phase of the last pressure reduction step. The pre-separation column preferably has from 5 to 20 theoretical separation stages in the stripping section and less than 3 theoretical separation stages in a rectifying section and is most preferably operated without reflux and without a rectifying section to minimize the residence time of propene oxide in the pre-separation column. The pre-separation column is preferably operated at a pressure of 0.16 to 0.3 MPa. Propene oxide and methanol are condensed from the overhead product of the pre-separation column and propene is preferably stripped from the resulting condensate in a propene stripping column which provides a bottom stream comprising propene oxide and methanol which is essentially free of propene. A purified propene oxide is preferably separated from the bottoms stream of the propene stripping column in an extractive distillation using water as the extraction solvent. The extractive distillation is preferably operated with additional feeding of a reactive compound containing an unsubstituted $NH_2$ group and capable of reacting with acetaldehyde during the extractive distillation, as described in WO 2004/048335. Extractive distillation with a reactive compound provides a high purity propene oxide containing less than 50 ppm of carbonyl compounds. Methanol can be recovered from the bottoms product of the pre-separation column by distillation. Preferably, the bottoms product of the pre-separation column is subjected to a catalytic hydrogenation with hydrogen to remove non-reacted hydrogen peroxide remaining from step a), as described in WO 03/093255, before methanol is separated by distillation. Such catalytic hydrogenation also reduces the amount of carbonyl compounds in the methanol separated by distillation, which is advantageous when the methanol is recycled to the reaction of step a). The bottoms product of the extractive distillation is preferably combined with the bottoms product of the pre-separation column, preferably before subjecting it to hydrogenation, in order to recover methanol. The recovered methanol can be recycled as solvent to the reaction of step a). Preferably, the recovered methanol or the bottoms product of the pre-separation column, optionally combined with bottoms product of the extractive distillation and preferably after a catalytic hydrogenation, is treated to remove organic nitrogen compounds as described in WO 2004/048354, more preferably by subjecting it to an acid treatment.

In a preferred embodiment of the process of the invention, the liquid reaction mixture from step a) is heated to a constant temperature in the range of from 35 to 70° C. before or during stripping it in step b). This embodiment is particularly advantageous when the reaction temperature used in step a) is increased over time in order to compensate for deactivation of the epoxidation catalyst, as it allows to operate steps c) and d) at essentially constant operating conditions despite the gradual increase in the temperature of the liquid reaction mixture from step a). Such heating of the liquid reaction mixture from step a) may also be used to increase the fraction of non-reacted propene in the strip gas stream and to reduce the amount of propene that has to be recovered from the stripped liquid reaction mixture, which can be used to reduce the energy needed for recompressing propene after work-up by pressure reduction.

In another preferred embodiment of the process of the invention, step a) is carried out at reaction conditions which provide a two phase liquid reaction mixture comprising a propene rich liquid phase and a liquid reaction mixture rich in water. This can be achieved by carrying out the epoxidation reaction of step a) at a pressure that is higher than the vapor pressure of propene at the reaction temperature, using an excess of propene sufficient to maintain an additional liquid phase rich in propene. The propene rich liquid phase and the liquid reaction mixture rich in water are then separated and the separated liquid reaction mixture rich in water is stripped in step b). When propene contained in the strip gas stream is separated by condensation, as described further above, the resulting condensate may be combined with the propene rich liquid phase for further work-up. When a propene distillation column as described further above is used for work-up, the propene rich liquid phase is preferably passed to this column for separating propene from higher boiling components contained in the propene rich liquid phase.

In yet another preferred embodiment of the process of the invention, step a) is carried out with a heterogeneous epoxidation catalyst in a trickle bed reactor, inert gas is fed to the trickle bed reactor and a purge gas stream comprising inert gas and oxygen is withdrawn from the trickle bed reactor. The purge gas stream withdrawn from the trickle bed reactor is preferably combined with the strip gas stream between steps b) and c). The inert gas fed to the trickle bed reactor is preferably the same as the inert gas used in step b). The amount of inert gas fed to the trickle bed reactor is preferably selected to provide an oxygen concentration in the purge gas stream in the range of from 0.1 to 10% by weight, preferably of from 0.5 to 8% by weight. Preferably, the oxygen concentration in the purge gas stream is measured continuously and the measured value is used to control the amount of inert gas fed to the trickle bed reactor in order to maintain an essentially constant oxygen concentration in the purge gas stream. This embodiment prevents formation of flammable gas mixtures in the epoxidation reactor when a trickle bed reactor is used in step a). No extra equipment is needed for recovering propene from the purge gas stream if the purge gas stream is combined with the strip gas stream between steps b) and c).

Figure 2:
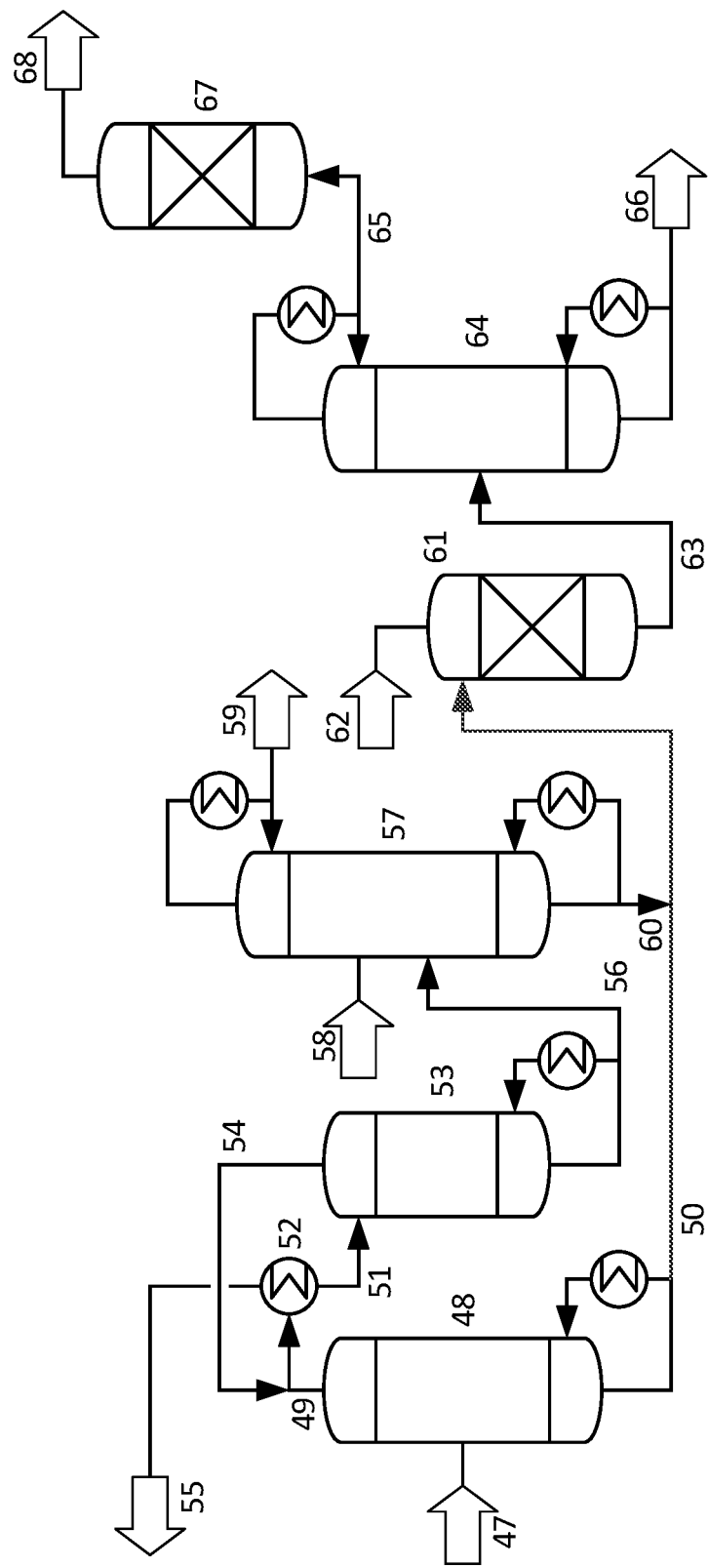

FIGS. 1 and 2 show a preferred embodiment of the process of the invention comprising epoxidation in a trickle bed reactor with a methanol solvent providing a two phase liquid reaction mixture comprising a propene rich liquid phase and a liquid reaction mixture rich in water, stripping of the liquid reaction mixture rich in water in a stripping column and condensation of propene oxide and part of the propene from the strip gas followed by absorption of propene into a methanol solvent.

A propene feed (1) is continuously reacted with hydrogen peroxide (2) in an epoxidation reactor (3) which contains a fixed bed of a titanium silicalite catalyst and is operated in trickle bed mode. The reaction is carried out in a methanol solvent (4) at a reaction pressure of 2.7 MPa. A nitrogen stream (5) is introduced into the epoxidation reactor (3) to maintain the reaction pressure and a purge gas stream (6) is withdrawn to prevent accumulation of oxygen in the reactor gas phase. The amount of propene feed (1) is chosen high enough to provide a liquid reaction mixture at the end of the catalyst fixed bed comprising two liquid phases, a propene rich liquid phase (7) and a liquid reaction mixture (8) rich in water and methanol which has a higher density than the propene rich liquid phase (7). The liquid reaction mixture (8), which contains dissolved oxygen from decomposition of hydrogen peroxide, is stripped with nitrogen (9) in a stripping column (10) at a pressure of 2.5 MPa. The stripped liquid reaction mixture (11), which is essentially free of oxygen, is heated in a heat exchanger (12) where a part of the propene dissolved in the stripped reaction mixture (11) is evaporated to form a vapor stream (13). The resulting liquid stream (14) is passed to a first flash evaporator (15) equipped with a demister (16) where the pressure is reduced to 0.7 MPa. The liquid phase (17) obtained in the first flash evaporator is passed to a second flash evaporator (18) equipped with a demister (19) where the pressure is further reduced to 0.13 MPa. The vapor phase (20) formed in the second flash evaporator (18) is compressed with a compressor (21), cooled in condenser (22) and the resulting stream (23) is passed to the first flash evaporator (15), where liquid from stream (23) combines with the liquid formed by depressurizing liquid (14) and vapor from stream (23) combines with the vapor phase formed by depressurizing liquid (14). The vapor phase (24) from first flash evaporator (15) is compressed with a compressor (25) and passed to a lower section of a distillation column C1 (26) operated at 2.1 MPa. A liquid recovered propene stream (27) is obtained from the column condenser (28) as the overhead product. The column bottoms (29) comprising propene oxide, methanol and dissolved propene are passed to the first flash evaporator (14). The strip gas stream (30) from the stripping column (10), which contains from 0.1 to 10% by weight of oxygen, is combined with the purge gas stream (6) and the combined stream is cooled in a condenser (31) to give a stripper condensate (32) and an off gas stream (33). Vapor stream (13), stripper condensate (32) and the propene rich liquid phase (7) are passed to the lower section of distillation column C1 (26) for recovering the propene contained in these streams.

A part (34) of the recovered propene stream (27) is passed to a distillation column C2 (35) operated at 2.1 MPa where propane is removed with the bottoms product (36) enriched in propane. The remaining part (37) of the recovered propene stream (27) is returned to reactor (3) as part of the propene feed (1). The propene starting material (38) is fed to distillation column C2 (35) near the column top and the overhead product (39) from the column condenser (40) is passed to epoxidation reactor (3) as part of the propene feed (1).

The off gas stream (33) from stripping column (10) and non-condensed gases (41, 42) from column condensers (28, 40) are passed to an absorption column (43), where propene is absorbed in a stream (44) of recovered methanol at a pressure of 1.9 MPa. The resulting methanol stream (45) loaded with propene is returned to epoxidation reactor (3) as part of the methanol solvent (4) and the off gas stream (46) depleted in propene is discharged.

The liquid phase (47) obtained in the second flash evaporator is passed to a pre-separation column (48), where it is separated by distillation to provide an overhead stream (49) comprising propene oxide, methanol and residual propene and a bottoms product (50) comprising methanol, water and non-reacted hydrogen peroxide. A liquid stream (51) comprising propene oxide and methanol is condensed in condenser (52) and propene is stripped from liquid stream (51) in the propene stripping column (53) with overhead stream (54), which is combined with overhead stream (49) of the pre-separation column. Propene is removed with the residual vapor (55) from condenser (52), which is returned to the second flash evaporator (18). The bottoms stream (56) from propene stripping column (53) is passed to propene oxide column (57) where it is subjected to an extractive distillation using an aqueous solution (58) comprising hydrazine as the extraction solvent. Purified propene oxide (59) is obtained as the overhead product.

The bottoms stream (60) from the propene oxide column, comprising water and methanol, is combined with bottoms product (50) from the pre-separation column and passed to a hydrogenation reactor (61) where it is hydrogenated with hydrogen (62) in the presence of a hydrogenation catalyst to remove non-reacted hydrogen peroxide and carbonyl compound by-products. The hydrogenated stream (63) is passed to methanol distillation column (64), where it is separated into a methanol overhead product (65) and a bottoms product (66) comprising water and by-products which is discharged. The methanol overhead product (65) is passed over a cation exchanger (67) in the hydrogen form for removing organic amine traces to provide a recovered methanol stream (68). Part or all of the recovered methanol stream (68) is passed as stream (44) to absorption column (43) and the remainder, combined with make-up methanol, is passed as stream (69) to epoxidation reactor (3).

Figure 3:
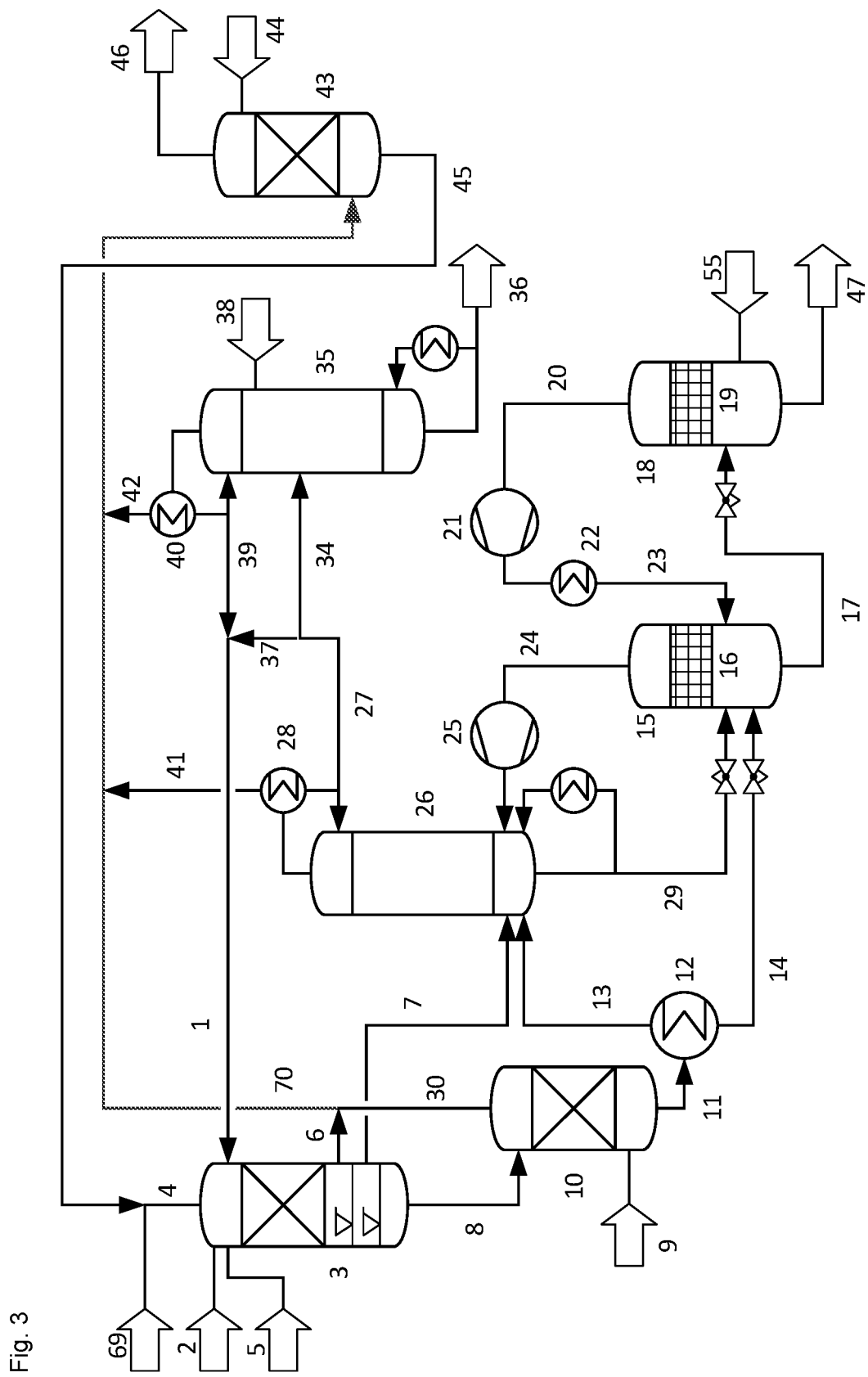
FIG. 3 shows an alternative preferred embodiment where no component is separated from the strip gas stream before propene is absorbed into the methanol solvent.

FIG. 3 shows an alternative preferred embodiment of the process of the invention where no component is separated from the strip gas stream before propene is absorbed into the methanol solvent.

In this second embodiment, the strip gas stream (30) from the stripping column (10) is combined with the purge gas stream (6) and the combined stream (70) is further combined with non-condensed gases (41, 42) from column condensers (28, 40) and passed to the absorption column (43) without separating any component before propene is absorbed into the methanol solvent in absorption column (43). The combined stream (70) contains more propene than the off gas stream (33) of the first embodiment. However, absorbing this larger amount of propene in absorption column (43) requires less additional equipment than condensing in condenser (31). Furthermore, a smaller distillation column C1 (26) can be used than in the first preferred embodiment and less energy is needed for operating distillation column C1 (26) because less propene is fed to this column than in the first preferred embodiment. All other steps of the second preferred embodiment are the same as in the first preferred embodiment.

LIST OF REFERENCE SIGNS

1 Propene feed
2 Hydrogen peroxide
3 Epoxidation reactor
4 Methanol solvent
5 Nitrogen stream
6 Purge gas stream
7 Propene rich liquid phase
8 Liquid reaction mixture rich in water and methanol
9 Nitrogen
10 Stripping column 11 Stripped liquid reaction mixture
12 Heat exchanger
13 Vapor stream from heat exchanger (12)
14 Liquid stream from heat exchanger (12)
15 First flash evaporator
16 Demister
17 Liquid phase obtained in first flash evaporator
18 Second flash evaporator
19 Demister
20 Vapor phase formed in second flash evaporator
21 Compressor
22 Condenser
23 Stream from condenser (22)
24 Vapor phase from first flash evaporator
25 Compressor
26 Distillation column C1
27 Recovered propene stream
28 Column condenser of distillation column C1
29 Column bottoms from distillation column C1
30 Strip gas
31 Condenser
32 Stripper condensate
33 Off gas stream
34 Part of recovered propene stream (27)
35 Distillation column C2
36 Bottoms product from distillation column C2
37 Remaining part of recovered propene stream (27)
38 Propene starting material
39 Overhead product of distillation column C2
40 Column condenser of distillation column C2
41 Non-condensed gas from column condenser (28)
42 Non-condensed gas from column condenser (40)
43 Absorption column
44 Stream of recovered methanol
45 Methanol stream loaded with propene
46 Off gas stream depleted in propene
47 Liquid phase obtained in second flash evaporator
48 Pre-separation column
49 Overhead stream from pre-separation column
50 Bottoms product from pre-separation column
51 Liquid stream comprising propene oxide and methanol
52 Condenser
53 Propene stripping column
54 Overhead stream from propene stripping column
55 Residual vapor from condenser (52)
56 Bottoms stream from propene stripping column
57 Propene oxide column
58 Aqueous solution comprising hydrazine
59 Purified propene oxide
60 Bottoms stream from propene oxide column
61 Hydrogenation reactor
62 Hydrogen
63 Hydrogenated stream
64 Methanol distillation column
65 Methanol overhead product from methanol distillation column
66 Bottoms product from methanol distillation column
67 Cation exchanger
68 Recovered methanol stream
69 Stream to epoxidation reactor (3)
70 Combined stream

The invention claimed is:

1. A process for the epoxidation of propene, comprising:
a) continuously reacting a propene feed with hydrogen peroxide in the presence of an epoxidation catalyst in a reaction step, using propene in excess to hydrogen peroxide, to provide a liquid reaction mixture comprising non-reacted propene;
b) stripping the liquid reaction mixture from step a) with an inert gas in a counter-current stripping column to provide an oxygen depleted stripped liquid reaction mixture and a strip gas stream, wherein the amount of inert gas used is selected so as to provide an oxygen concentration in the strip gas stream in the range of from 0.1 to 10% by weight;
c) separating non-reacted propene from the strip gas stream obtained in step b) and recycling it to step a); and
d) separating propene oxide from the stripped liquid reaction mixture obtained in step b).

2. The process of claim 1, wherein the amount of inert gas is selected to provide an oxygen concentration in the strip gas stream in the range of from 0.5 to 8% by weight.

3. The process of claim 1, wherein step a) is carried out at a reaction pressure of at least 1.9 MPa and step b) is carried out at a pressure in the range of from 80% to 110% of the reaction pressure.

4. The process of claim 1, wherein non-reacted propene is separated from the stripped liquid reaction mixture obtained in step b) and recycled to step a).

5. The process of claim 1, wherein the liquid reaction mixture is heated to a constant temperature in the range of from 35 to 70° C. before or during stripping it in step b).

6. The process of claim 1, wherein step a) is carried out under reaction conditions providing a two phase liquid reaction mixture comprising a propene rich liquid phase and a liquid reaction mixture rich in water, said propene rich liquid phase and said liquid reaction mixture rich in water are separated and the separated liquid reaction mixture rich in water is stripped in step b).

7. The process of claim 1, wherein in step c) the strip gas stream is contacted with a liquid solvent to absorb propene into said solvent, providing a propene depleted gas stream and a propene loaded solvent, and said propene loaded solvent is passed to step a).

8. The process of claim 7, wherein in step c) propene oxide is separated from the strip gas stream by partial condensation before said stream is contacted with said liquid solvent.

9. The process of claim 7, wherein in step c) part of the propene contained in the strip gas stream is separated by condensation before said stream is contacted with said liquid solvent.

10. The process of claim 7, wherein no component is separated from the strip gas stream before contacting it with said liquid solvent.

11. The process of claim 1, wherein step a) is carried out with a heterogeneous epoxidation catalyst in a trickle bed reactor, inert gas is fed to said trickle bed reactor, a purge gas stream comprising inert gas and oxygen is withdrawn from said trickle bed reactor and said purge gas stream is combined with the strip gas stream between steps b) and c).

12. The process of claim 1, wherein the inert gas is selected from nitrogen, argon, oxygen depleted air, methane and mixtures thereof.

13. The process of claim 1, wherein step a) is carried out with a titanium zeolite catalyst in the presence of a solvent selected from the group consisting of: methanol, ethanol, tert-butanol, ethylene glycol, 1,2-propanediol, 1,3-propanediol, tetrahydrofuran, dioxane, ethylene glycol monomethyl ether, ethylene glycol monoethyl ether, ethylene glycol monobutyl ether, propylene glycol monomethyl ethers, acetone, 2-butanone, acetonitrile and propionitrile.

14. The process of claim 13, wherein step a) is carried out with a titanium silicalite catalyst in the presence of a methanol solvent.

15. The process of claim 10, wherein step a) is carried out at a reaction pressure of at least 1.9 MPa and step b) is carried out at a pressure in the range of from 80% to 110% of the reaction pressure.

16. The process of claim 10, wherein the amount of inert gas is selected to provide an oxygen concentration in the strip gas stream in the range of from 0.5 to 8% by weight.

17. The process of claim 10, wherein step a) is carried out with a heterogeneous epoxidation catalyst in a trickle bed reactor, inert gas is fed to said trickle bed reactor, a purge gas stream comprising inert gas and oxygen is withdrawn from said trickle bed reactor and said purge gas stream is combined with the strip gas stream between steps b) and c).

18. The process of claim 11, wherein step a) is carried out with a titanium zeolite catalyst in the presence of a solvent selected from the group consisting of methanol, ethanol, tert-butanol, ethylene glycol, 1,2-propanediol, 1,3-propanediol, tetrahydrofuran, dioxane, ethylene glycol monomethyl ether, ethylene glycol monoethyl ether, ethylene glycol monobutyl ether, propylene glycol monomethyl ethers, acetone, 2-butanone, acetonitrile and propionitrile.

19. The process of claim 17, wherein step a) in the process is carried out with a titanium silicalite catalyst in the presence of a methanol solvent.

20. The process of claim 19, wherein the amount of inert gas is selected to provide an oxygen concentration in the strip gas stream in the range of from 0.5 to 8% by weight.

* * * * *